(12) United States Patent
Zhao

(10) Patent No.: US 7,407,647 B2
(45) Date of Patent: Aug. 5, 2008

(54) ORGANIC RADIOGRAPHIC CONTRASTING AGENTS FOR MEDICAL DEVICES

(75) Inventor: Jonathon Z. Zhao, Belle Mead, NJ (US)

(73) Assignee: Cordis Corporation, Miami Lakes, FL (US)

( * ) Notice: Subject to any disclaimer, the term of this patent is extended or adjusted under 35 U.S.C. 154(b) by 51 days.

(21) Appl. No.: 11/296,606

(22) Filed: Dec. 7, 2005

(65) Prior Publication Data

US 2007/0128120 A1 Jun. 7, 2007

(51) Int. Cl.
*A61K 49/04* (2006.01)
(52) U.S. Cl. .......................................... 424/9.4; 424/9.4
(58) Field of Classification Search .................... 424/9.4
See application file for complete search history.

(56) References Cited

U.S. PATENT DOCUMENTS

| | | | |
|---|---|---|---|
| 3,734,953 A * | 5/1973 | Bernstein et al. | 562/442 |
| 4,873,075 A * | 10/1989 | Counsell et al. | 424/1.85 |
| 5,451,393 A * | 9/1995 | Liversidge et al. | 424/9.45 |
| 6,426,145 B1 | 7/2002 | Moroni | |
| 6,599,448 B1 * | 7/2003 | Ehrhard et al. | 252/582 |
| 6,852,308 B2 | 2/2005 | Kohn | |

FOREIGN PATENT DOCUMENTS

| EP | 0557345 A | 9/1993 |
|---|---|---|
| EP | 1702628 A | 9/2006 |

OTHER PUBLICATIONS

Wang J. S. et al.: "In vitro and in vivo biological responses to a novel radiopacifying agent for bone cement" J. Roy. Soc. Interface, vol. 2, No. 2, Mar. 2005, pp. 71-78 XP002461899.
Kjellson F. et al.: "Tensile properties of a bone cement containing non-ionic contrast media" Journal of Material Science, vol. 12, No. 10-12, 2001, pp. 889-894 XP009013837.

* cited by examiner

*Primary Examiner*—Michael G. Hartley
*Assistant Examiner*—Melissa Perreira

(57) ABSTRACT

The present invention discloses an organic radiographic contrasting agent containing an aliphatic or alicyclic backbone and multiple halogen-substituted aromatic groups. Each of the halogen-substituted aromatic groups in the radiographic contrasting agent is substituted with at least three halogen atoms and is covalently attached to the aliphatic or alicyclic backbone. The present invention also discloses a radio-opaque polymeric material comprising the radiographic contrasting agent and at least one polymer. The radiographic contrasting agent is physically admixed with the at least one polymer or physically embedded or dispersed in the at least one polymer. The radio-opaque polymeric material provides enhanced contrasting intensity in radiographic imaging. The radio-opaque polymeric material can be applied on at least a portion of one surface of a medical device. The radio-opaque polymeric material can also be used to construct a medical device, a component thereof, or a portion of a component thereof.

2 Claims, No Drawings

ORGANIC RADIOGRAPHIC CONTRASTING AGENTS FOR MEDICAL DEVICES

FIELD OF INVENTION

The present invention relates to an organic contrasting agent that provides enhanced contrasting intensity in radiographic imaging of medical devices and a polymeric material containing the organic contrasting agent and at least one polymer.

BACKGROUND OF INVENTION

It is important that medical devices are biocompatible since most medical devices interface with biological tissues during use. Therefore, medical devices are preferred to be prepared from biocompatible materials. More specifically, the ideal materials for medical devices should satisfy at least the following requirements: (1) conformable, i.e., conform to the biological structure without inducing detrimental stress, (2) robust, i.e., withstand handling during fabrication and implantation, and (3) chemically inert to body tissue and body fluids. However, conventional materials used for the construction of medical devices, such as stainless steel and other alloys, not only are physically rigid, but also cause inflammatory reactions or other side effects when interfacing with biological tissues.

To overcome these problems, synthetic polymeric materials, including both biodegradable and non-biodegradable polymers, have been widely used to fabricate medical devices. Common biodegradable polymers include polylactide (PLA) polyglycolide (PGA), poly(lactide-co-glycolide) (PLGA), polycaprolactone (PCL), polyphosphoesters (PPE), polyorthoesters, polyanhydrides, polyphosphazene, poly(esteramide) (PEA), and copolymers and mixtures thereof. Non-biodegradable polymers are also known as nonabsorbable polymers. Common nonabsorbable polymeric materials include, but are not limited to: silicone elastomers, polyutheranes, polymethyl methacrylate, Dacron®, Teflon®, and derivatives thereof. However, these polymeric materials are not radio-opaque. Consequently, medical devices made from these polymers cannot be visualized by means of radiographic imaging. The ability to see the radiographic image of a medical device being used in, or implanted within, the body is very important since radiographic imaging provides a physician the ability to monitor and adjust the medical device during operation. For some medical implant applications, X-ray visibility is mandatory.

To achieve desirable radio-opacity in the polymeric materials used for medical implants, one conventional method utilizes inorganic radiographic contrasting agents, such as barium sulfate, zirconium dioxide, or bismuth halides as additives or fillers in the polymeric material to form a radio-opaque polymeric matrix. However, these inorganic agents do not mix well with polymeric materials and may cause phase separation or even clumps in the radio-opaque polymeric matrix. The phase separation problem is further aggravated since high concentrations (around 10%, and often times 20-30% by weight) of these inorganic radiographic contrasting agents are routinely used to obtain the required radio-opacity. The incompatibility between the polymeric and inorganic phases compromises the physicomechanical properties (e.g., lubricity and robustness) of the polymer matrix. Another disadvantage of using inorganic radiographic contrasting agents is the leach-out of these inorganic agents from the radio-opaque polymeric matrix, which adversely compromises the mechanical strength of the polymeric material.

An alternative approach to introduce radio-opacity into polymeric materials is to synthesize polymers having covalently bound bromine or iodine atoms that may produce a radiographic contrasting effect (See U.S. Pat. No. 6,426, 145). One radio-opaque composition of the prior art comprises a polymer having a non-leachable radio-opaque moiety covalently attached to the polymer (See U.S. Pat. No. 6,599, 448), wherein the non-leachable radio-opaque moiety includes halogen substituted aromatic groups. The prior art has also disclosed a radio-opaque polymeric material comprising a diphenol-based monomer unit substituted with at least one bromine or iodine atom (See U.S. Pat. No. 6,852, 308). However, preparations of these prior art radio-opaque polymers require synthesis of radiographic contrasting monomer units, which may increase the technical complexity and production cost.

Thus, there remains a need for a radiographic contrasting agent that is compatible with polymeric materials and provides enhanced contrasting intensity as well.

SUMMARY OF THE INVENTION

Accordingly, the present invention provides a radiographic contrasting agent comprising an aliphatic or alicyclic backbone of 2 to 12 carbon atoms and at least two halogen-substituted aromatic groups, wherein each of the at least two halogen-substituted aromatic groups is substituted with at least three halogen atoms, and is covalently attached to the aliphatic or alicyclic backbone through a linkage group, wherein the linkage group is selected from the group consisting of oxygen, sulfur, —NH—, —O(CO)—, —(CO)O—, —NH(CO)—, —(CO)NH—, —O($SO_2$)—, —($SO_2$)O—, —O(SO)—, —(SO)O—, —NH($SO_2$)—, —($SO_2$)NH—, —NH(SO)—, —(SO)NH—, and triazole. Preferably, the inventive radiographic contrasting agent comprises at least three halogen-substituted aromatic groups.

The present invention also provides a radio-opaque polymeric material comprising an organic radiographic contrasting agent and at least one polymer, wherein the organic radiographic contrasting agent is physically admixed with the at least one polymer or physically embedded or dispersed in the at least one polymer, and the organic radiographic contrasting agent comprises an aliphatic or alicyclic backbone of 2 to 12 carbon atoms and at least two halogen-substituted aromatic groups, wherein each of the at least two halogen-substituted aromatic groups is substituted with at least three halogen atoms, and is covalently attached to the aliphatic or alicyclic backbone through a linkage group, wherein the linkage group is selected from the group consisting of oxygen, sulfur, —NH—, —O(CO)—, —(CO)O—, —NH(CO)—, —(CO) NH—, —O($SO_2$)—, —($SO_2$)O—, —O(SO)—, —(SO)O—, —NH($SO_2$)—, —($SO_2$)NH—, —NH(SO)—, —(SO)NH—, and triazole. The at least one polymer may be at least one biodegradable polymer, at least one non-biodegradable polymer, or a mixture thereof.

In another aspect, the present invention provides a medical device, wherein at least one portion of the medical device is radio-opaque, the at least one radio-opaque portion of the medical device comprising a radio-opaque polymeric material, which comprises a radiographic contrasting agent and at least one polymer, wherein the radiographic contrasting agent comprises an aliphatic or alicyclic backbone of 2 to 12 carbon atoms and at least two halogen-substituted aromatic groups, wherein each of the at least two halogen-substituted aromatic groups is substituted with at least three halogen atoms, and is covalently attached to the aliphatic or alicyclic backbone through a linkage group, wherein the linkage group is selected from the group consisting of oxygen, sulfur, —NH—, —O(CO)—, —(CO)O—, —NH(CO)—, —(CO)NH—, —O(SO$_2$)—, —(SO$_2$)O—, —O(SO)—, —(SO)—, —NH(SO$_2$)—, —(SO$_2$)NH—, —NH(SO)—, —(SO)NH—, and triazole. Preferably, the medical device is an implantable medical device. More preferably, the medical device is a cardiovascular or peripheral drug eluting stent.

DETAILED DESCRIPTION OF THE INVENTION

The present invention provides a radiographic contrasting agent, comprising an aliphatic or alicyclic backbone of 2 to 12 carbon atoms and at least two halogen-substituted aromatic groups. As used herein, "an aliphatic backbone" denotes an organic moiety consisting of carbon atoms linked in open chains, and "an alicyclic backbone" denotes an organic moiety consisting of carbon atoms forming one or more rings that are not aromatic. Each of the at least two halogen-substituted aromatic groups in the inventive radiographic contrasting agent is substituted with at least three halogen atoms and is covalently attached to the aliphatic or alicyclic backbone through a linkage group. The linkage group is selected from oxygen, sulfur, —NH—, —O(CO)—, —(CO)O—, —NH(CO)—, —(CO)NH—, —O(SO$_2$)—, —(SO$_2$)O—, —O(SO)—, —(SO)O—, —NH(SO$_2$)—, —(SO$_2$)NH—, —NH(SO)—, —(SO)NH—, or triazole. As used herein, "(CO)" denotes a carbonyl moiety; "(SO)" denotes a sulfinyl moiety; and "(SO$_2$)" denotes a sulfonyl moiety. The linkage group links the aliphatic or alicyclic backbone and the at least two halogen-substituted aromatic groups through covalent bonds. The linkage group expressed as "-linkage-" denotes a linkage in the manner as follows: (the aliphatic or alicyclic backbone)-linkage-(one of the at least two halogen-substituted aromatic groups). For example, "—(CO)O—" denotes a linkage as follows: (the aliphatic or alicyclic backbone)—(CO)O— (one of the at least two halogen-substituted aromatic groups). Preferably, the linkage group of the present invention is —NH(CO)—, —O(CO)—, or triazole. The term "triazole" as used herein includes both 1,2,3-triazole and 1,2,4-triazole. When the linkage group is triazole, the aliphatic or alicyclic backbone and the at least two halogen-substituted aromatic group are linked through one of the two carbon atoms, and the nitrogen atom at the 4 position in the case of 1,2,4-triazole or the nitrogen atom at the 3 position in the case of 1,2,3-triazole.

The aliphatic backbones suitable for the present invention include, but are not limited to: ethyl, n-propyl, isopropyl, n-butyl, sec-butyl, n-pentyl, n-hexyl, n-heptyl, n-octyl, and analogs or isomers thereof. The alicyclic backbones suitable for the present invention include, but are not limited to: cyclobutyl, cyclopentyl, cyclohexyl, cycloheptyl, cyclooctyl, cyclobutene, cyclopentene, cyclohexene, cycloheptene, cyclooxtanene, and analogs or isomers thereof. Preferably, the aliphatic or alicyclic backbone is an aliphatic or alicyclic moiety having 4 to 8 carbon atoms.

It is preferable that the radiographic contrasting agent of the present invention contains at least three halogen-substituted aromatic groups. By "a halogen-substituted aromatic group", it is meant an aromatic group having at least one halogen substituent. By "an aromatic group", it is meant a cyclic organic compound containing multiple conjugated double bonds. The halogen-substituted aromatic group of the present invention may be halogen-substituted carbocyclic, heterocyclic, or polycyclic compounds. Halogen-substituted aromatic groups suitable for the present invention include, but are not limited to: halogen-substituted benzene, toluene, xylenes, styrenes, pyridine, furan, naphthalene, anthracene, phenanthrene, indole, quinoline, and isoquinoline. Preferably, the halogen-substituted aromatic group of the present invention is halogen-substituted benzene. Each of the halogen-substituted aromatic groups of the present invention is substituted with at least three halogen atoms. Preferably, the at least three halogen atoms are bromine, iodine, or combinations thereof. More preferably, the halogen-substituted aromatic group of the present invention is substituted with at least three iodine atoms. In one preferred embodiment of the present invention, the halogen-substituted aromatic group is 2,3,5-triiodobenzene.

The radiographic contrasting agent of the present invention can be prepared through reactions between an organic compound containing a polyhydric alcohol or a polyamine and an halogen-substituted aromatic compound. The organic compounds containing the polyhydric alcohol or polyamine suitable for the present invention include, but are not limited to: ethylene glycol, propylene glycol, glycerol, pentaerythritol, trethelose, sorbitol, mannitol, xylitol, putrescine, spermidine, spermine, and analogs thereof. The radiographic contrasting agent of the present invention may also be prepared by other methods known to one skilled in the art.

In one embodiment of the present invention, the organic radiographic contrasting agent has the following structure:

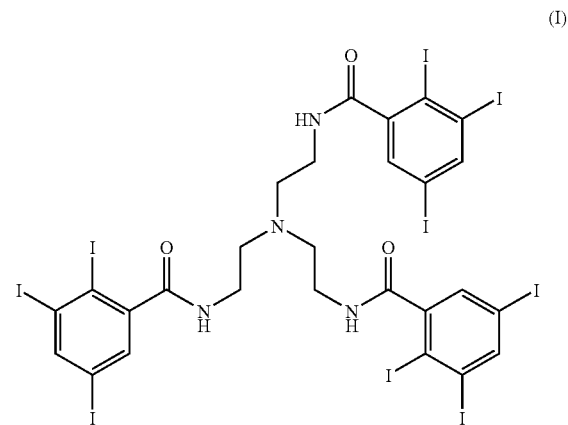

(I)

In another embodiment of the present invention, the organic radiographic contrasting agent has the following structure:

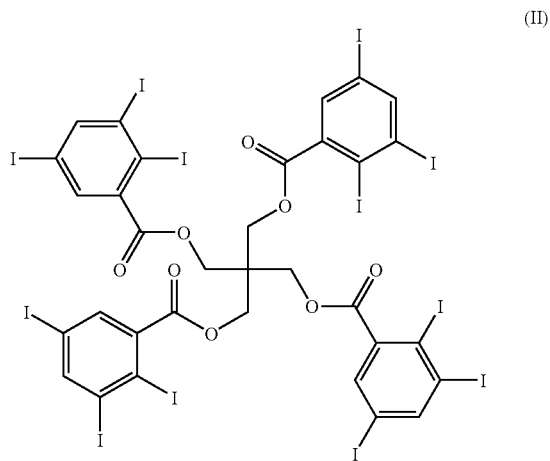

(II)

The inventive radiographic contrasting agent of formula (II) is synthesized through a reaction between pentaerythritol and 2,3,5-triiodobenzoic acid in the presence of thionyl chloride, i.e., SOCl$_2$, as shown in Scheme 1.

Scheme 1:

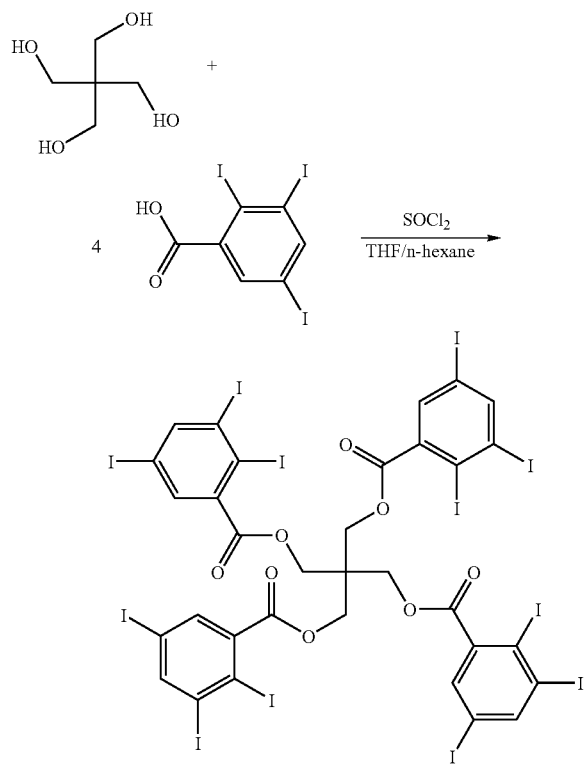

The inventive radiographic contrasting agent is sparsely soluble in water and substantially soluble in common organic solvents. By "substantial soluble", it is meant having a solubility of about 10 mg per milliliter or above. By "sparsely soluble", it is meant having a solubility of about 1 mg per milliliter or below. Particularly, unlike the inorganic radiographic contrasting agents, the inventive radiographic contrasting agent readily dissolves or disperses in organic solvents used to dissolve various polymers, such as dimethylacetamide (DMAC), dimethylformide (DMF), N-methylpyrrolidone (NMP), dimethylsulfoxide (DMSO), tetrahydrofuran (THF), 1,4-dioxane, and chlorinated solvents (e.g., dichloromethane). Thus, the inventive radiographic contrasting agent is miscible with various polymers used for the construction of medical devices. Due to its sparse solubility in water, the inventive radiographic contrasting agent does not swell the polymer matrices resulted from physically admixing the inventive radiographic contrasting agent and one or more polymers. The inventive radiographic contrasting agent only leaches out of the polymer matrices in such a very slow process that the mechanical strength and/or the degradation profile of the polymer matrices are not adversely compromised. Furthermore, when the inventive radiographic contrasting agent is admixed with one or more polymers, the inventive radiographic contrasting agent does not form any clumps or cause any phase separation in the resulting polymer matrices. Therefore, the polymer matrices of the inventive radiographic contrasting agent and one or more polymers retain the smoothness and lubricity of the one or more polymers. Moreover, the polymer matrices of the inventive radiographic contrasting agent and one or more polymers either retain the mechanical strength of the one or more polymers or show enhanced mechanical strength. In addition, the inventive radiographic contrasting agent contains multiple halogen atoms in a small, single organic compound resulting in a very high contrasting intensity. Thus, a comparatively small quantity of the inventive radiographic contrasting agent in polymer matrices is able to impart sufficient image quality, and consequently the polymer matrices have more capacity to load therapeutic agents or other functional molecules.

The present invention also provides a radio-opaque polymeric material comprising a radiographic contrasting agent and at least one polymer. The radiographic contrasting agent in the inventive radio-opaque polymeric material is physically admixed with the at least one polymer or physically embedded or dispersed in the at least one polymer. The radiographic contrasting agent comprises an aliphatic or alicyclic backbone of 2 to 12 carbon atoms and at least two halogen-substituted aromatic groups, wherein each of the at least two halogen-substituted aromatic groups is substituted with at least three halogen atoms, and each of the at least two halogen-substituted aromatic groups is covalently attached to the aliphatic or alicyclic backbone through a linkage group, wherein the linkage group is selected from the group consisting of oxygen, sulfur, —NH—, —O(CO)—, —(CO)O—, —NH(CO)—, —(CO)NH—, —O(SO$_2$)—, —(SO$_2$)O—, —O(SO)—, —(SO)O—, —NH(SO$_2$)—, —(SO$_2$)NH—, —NH(SO)—, —(SO)NH—, and triazole. Preferably, the radiographic contrasting agent of the present invention comprises at least three halogen-substituted aromatic groups.

The at least one polymer of the present invention may be any polymer compatible with the inventive radiographic contrasting agent. Preferably, the at least one polymer may be at least one biodegradable polymer, at least one non-biodegradable polymer, or a mixture thereof. By "biodegradable polymer", it is meant a polymer that can be degraded or decomposed by natural biological processes, as by the action of bacteria, plants, or animals. Biodegradable polymers are also known as bioabsorbable polymers or biodissolvable polymers. Biodegradable polymers suitable for the present invention include, but are not limited to: polyglycolide, polylactide, poly(lactide-co-glycolide), polydioxanone, polycaprolactone, polyhydroxybutyrate, poly(trimethylene carbonate), polyphosphoesters (PPE), polyorthoesters, polyanhydrides, polyphosphazene, poly(ester amide), and copolymers and mixtures thereof. Non-biodegradable polymers suitable for the present invention include, but are not limited to: silicone elastomers, poly(ethylene-co-vinyl acetate), polyacrylates, polymethacrylates, polyethylene oxide, polystyrene, polyurethanes, polyamides, and copolymers and mixtures thereof.

The inventive radiographic contrasting agent may be physically admixed with the at least one polymer or physically embedded or dispersed in the at least one polymer in any manner known to one skilled in the art. In one embodiment of the present invention, the inventive radiographic contrasting agent is dissolved in an organic solvent, and the resulting solution is then admixed with a solution of at least one polymer in the organic solvent. In another embodiment of the present invention, the inventive radiographic contrasting agent is directly dissolved in a solution of at least one polymer in an organic solvent.

The weight ratio of the inventive radiographic contrasting agent to the at least one polymer varies depending upon the structure of the inventive radiographic contrasting agent and the desired radio-opacity of the polymeric material. Typically, the weight ratio of the inventive radiographic contrasting agent to the at least one polymer is less than about 20:100. Preferably, the weight ratio of the inventive radiographic contrasting agent to the at least one polymer is less than about 10:100.

The inventive radio-opaque polymeric material not only possesses the desirable biocompatibility and physicomechanical properties (e.g., strength, fatigue, smoothness), but also has radio-opacity for visualization in radiographic imaging. The mechanical strength and/or the degradation time of the radio-opaque polymeric material can be tuned by adjusting the molecular weight or composition of the at least one polymer. The radiographic contrast intensity of the inventive biodegradable polymer can be adjusted by varying the ratio of the inventive radiographic contrasting agent and the at least one polymer. The inventive radiographic contrasting agent is soluble in organic solvents and miscible with the bulk polymeric materials used to construct a medical device. Therefore, the inventive radio-opaque polymeric material is suitable for medical devices, particularly those interfacing with biological tissues, such as implantable medical devices.

In another aspect, the present invention provides a medical device, wherein at least one portion of the medical device is radio-opaque, the at least one radio-opaque portion of the medical device comprising a radio-opaque polymeric material, which comprises a radiographic contrasting agent and at least one polymer, wherein the radiographic contrasting agent is physically admixed with the at least one polymer or physically embedded or dispersed in the at least one polymer, and the radiographic contrasting agent comprises an aliphatic or alicyclic backbone of 2 to 12 carbon atoms and at least two halogen-substituted aromatic groups, wherein each of the at least two halogen-substituted aromatic groups is substituted with at least three halogen atoms, and is covalently attached to the aliphatic or alicyclic backbone through a linkage group, wherein the linkage group is selected from the group consisting of oxygen, sulfur, —NH—, —O(CO)—, —(CO)O—, —NH(CO)—, —(CO)NH—, —O($SO_2$)—, —($SO_2$)O—, —O(SO)—, —(SO)O—, —NH($SO_2$)—, —($SO_2$)NH—, —NH(SO)—, —(SO)NH—, and triazole.

In the present invention, the radio-opaque portion of the medical device may be at least a portion of one surface of the medical device, a component of the medical device, or a portion of a component of the medical device. The radio-opaque portion of the medical device may be in any shape or size depending upon the intended use and the fabrication method of the medical device. When all surfaces of the medical device are coated with the inventive radio-opaque biodegradable polymeric material or the whole medical device is prepared from the inventive radio-opaque biodegradable polymeric material, the whole medical device is radio-opaque. Preferably, the medical device of the present invention is an implantable medical device. More preferably, the implantable medical device is a cardiovascular or peripheral drug eluting stent. Examples of the medical devices suitable for the present invention include, but are not limited to: wound closure devices, such as, sutures, staples, and mesh; orthopedic fixation devices, such as, bone fracture fixation implants and bone augmentation implants; intestinal devices, such as, anastomosis rings and ligating clips; cardiovascular devices, such as, vascular grafts, and cardiovascular or peripheral drug elution stents; dental implants; nerve growth conduits; guiding wires, catheters, and other implantable medical devices. The inventive radio-opaque biodegradable polymeric material may be applied on at least a portion of one surface of a medical device as a coating using cast, spray, spin, dipping, or other methods known to one skilled in the art. The medical device or a component thereof can be constructed from the inventive radio-opaque biodegradable polymeric material using solvent casting, injection molding, compression molding, extrusion, or other methods know to one skilled in the art to construct polymeric medical devices.

The following non-limiting example is provided to further illustrate the present invention. Because the example is provided for illustrative purpose only, the invention embodied therein should not be limited thereto.

EXAMPLE

Synthesis of a Radiographic Contrasting Agent of Formula (I)

The inventive radiographic contrasting agent of formula (I) was prepared through the synthetic route as shown in Scheme 2:

Scheme 2:

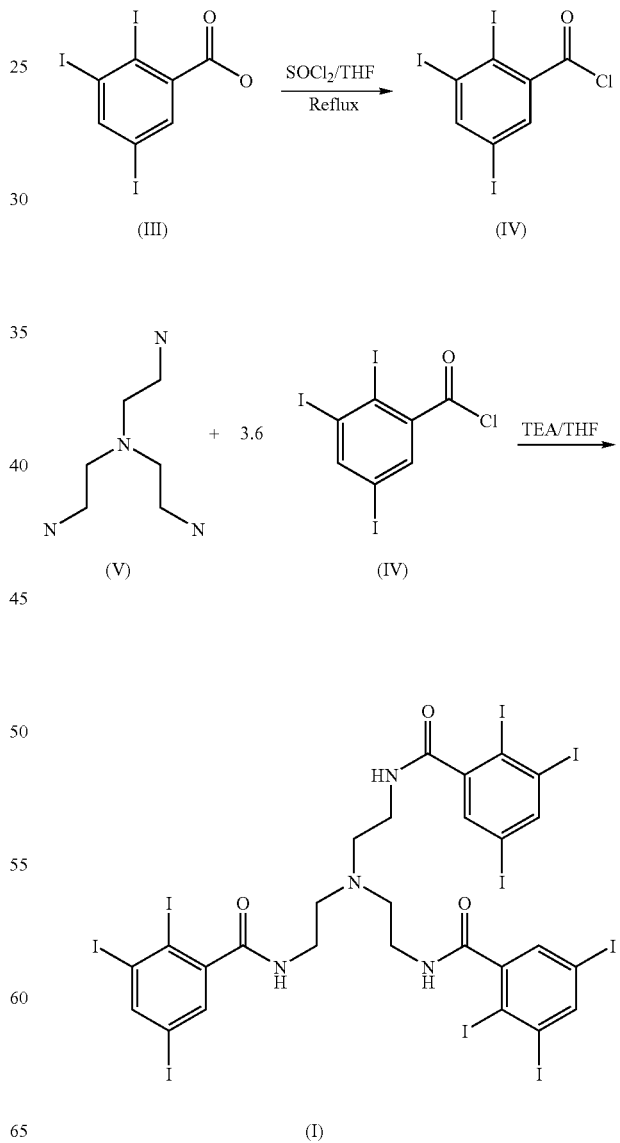

(I)

A mixture of compound (III) (40 g, 0.08 mol) and thionyl chloride (20 g, 0.017 mol) in THF (300 mL) was heated to reflux for 40 minutes. Then the solvent was removed by a rotavapor. The resulting dry solid was re-crystallized in hexane. This process provided 20 g of compound (IV), which had a yield of 49%.

To a solution of compound (V) (4.06 g, 0.028 mol) in THF (400 mL) and triethylamine (16 mL), i.e., TEA, was slowly added a solution of compound (IV) (51.8 g, 0.1 mol) in THF (150 mL) at 0° to 5° C. in a period of 10 to 15 minutes. The resulting reaction mixture was then stirred at room temperature for 2 hours. Next, the reaction mixture was added to 1000 mL of water. The solid was collected by filtration, washed with saturated sodium carbonate (3×100 mL), water (3×100 mL), and warm methanol (3×100 mL, 45-50° C.). Compound (IV) (43 g) was obtained with a yield of 96% and a purity of above 95% (determined by $H^1$NMR). $H^1$NMR (DMSO-$d_6$): 8.39(s, 3H); 8.26(s, 3H); 7.56(s, 3H); 3.36(br, 6H); 2.69(br, 6H). MS(+): 1592; MS(−): 1590.

While the present invention has been particularly shown and described with respect to preferred embodiments thereof, it will be understood by those skilled in the art that the foregoing and other changes in forms and details may be made without departing from the spirit and scope of the invention. It is therefore intended that the present invention not be limited to the exact forms and details described and illustrated but fall within the scope of the appended claims.

Having thus described in our invention in detail, what is claimed as new and is desired to be secured by the Letters Patent is:

1. A radiographic contrast agent, having the following structure:

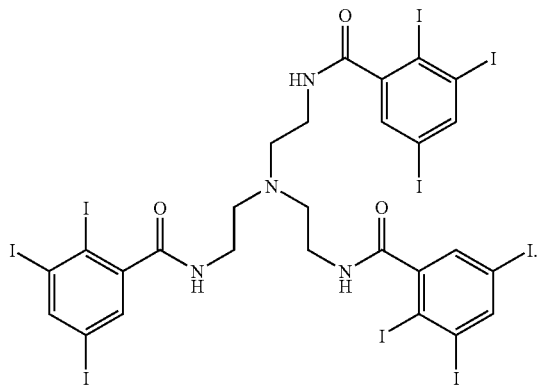

2. A radiographic contrast agent, having the following structure:

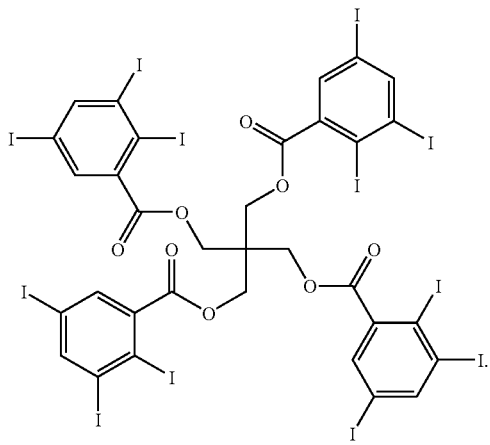

* * * * *